United States Patent
Kawaguchi

(10) Patent No.: US 10,568,906 B2
(45) Date of Patent: Feb. 25, 2020

(54) COMPOSITION FOR IMPROVING NUTRITIONAL STATUS, REDUCING FREQUENCY OF FEVER AND/OR INCREASING IMMUNOCOMPETENCE OF THE ELDERLY

(75) Inventor: Susumu Kawaguchi, Meguro-ku (JP)

(73) Assignee: NUTRI CO., LTD., Mie (JP)

( * ) Notice: Subject to any disclaimer, the term of this patent is extended or adjusted under 35 U.S.C. 154(b) by 0 days.

(21) Appl. No.: 12/811,909

(22) PCT Filed: Jan. 6, 2009

(86) PCT No.: PCT/JP2009/050018
§ 371 (c)(1),
(2), (4) Date: Jul. 7, 2010

(87) PCT Pub. No.: WO2009/087987
PCT Pub. Date: Jul. 16, 2009

(65) Prior Publication Data
US 2010/0278799 A1  Nov. 4, 2010

(30) Foreign Application Priority Data
Jan. 10, 2008  (JP) ................................ 2008-003072

(51) Int. Cl.
| | |
|---|---|
| A61K 33/30 | (2006.01) |
| A61P 37/00 | (2006.01) |
| A61P 43/00 | (2006.01) |
| A61K 9/00 | (2006.01) |
| A61K 9/06 | (2006.01) |
| A61K 31/355 | (2006.01) |
| A61K 31/375 | (2006.01) |
| A61K 31/4415 | (2006.01) |
| A61K 31/51 | (2006.01) |
| A61K 31/525 | (2006.01) |
| A61K 31/593 | (2006.01) |
| A61K 31/714 | (2006.01) |
| A61K 33/04 | (2006.01) |
| A61K 45/06 | (2006.01) |
| A61K 47/36 | (2006.01) |
| A61K 47/46 | (2006.01) |
| A23L 33/10 | (2016.01) |
| A23L 33/15 | (2016.01) |
| A23L 33/16 | (2016.01) |

(52) U.S. Cl.
CPC .............. *A61K 33/30* (2013.01); *A23L 33/10* (2016.08); *A23L 33/15* (2016.08); *A23L 33/16* (2016.08); *A61K 9/0095* (2013.01); *A61K 9/06* (2013.01); *A61K 31/355* (2013.01); *A61K 31/375* (2013.01); *A61K 31/4415* (2013.01); *A61K 31/51* (2013.01); *A61K 31/525* (2013.01); *A61K 31/593* (2013.01); *A61K 31/714* (2013.01); *A61K 33/04* (2013.01); *A61K 45/06* (2013.01); *A61K 47/36* (2013.01); *A61K 47/46* (2013.01); *A23V 2002/00* (2013.01)

(58) Field of Classification Search
CPC ...................... A61K 2300/00; A23V 2200/324
USPC ....................................................... 424/94.1
See application file for complete search history.

(56) References Cited

U.S. PATENT DOCUMENTS

| | | | |
|---|---|---|---|
| 5,556,644 A | 9/1996 | Chandra | 424/630 |
| 5,589,468 A * | 12/1996 | Lin et al. | 514/52 |
| 5,686,429 A | 11/1997 | Lin et al. | 514/52 |
| 5,904,948 A * | 5/1999 | Sartorio | A23F 5/38 426/453 |
| 6,846,494 B1 | 1/2005 | Verheul-Koot et al. | 424/439 |
| 6,929,793 B2 | 8/2005 | Spivey-Krobath et al. | 424/93.4 |
| 7,008,654 B1 | 3/2006 | Fuchs et al. | 426/72 |
| 2002/0146463 A1 | 10/2002 | Clayton | 424/617 |
| 2004/0005305 A1 | 1/2004 | Spivey-Krobath et al. | 424/93.45 |
| 2004/0131659 A1* | 7/2004 | Gibson et al. | 424/439 |
| 2005/0136129 A1 | 6/2005 | Verheul-Koot et al. | 424/638 |
| 2005/0208035 A1 | 9/2005 | Spivey-Krobath et al. | 424/93.45 |
| 2008/0020062 A1 | 1/2008 | Verheul-Koot et al. | 424/641 |

FOREIGN PATENT DOCUMENTS

| | | |
|---|---|---|
| CN | 1503632 A | 6/2004 |
| EP | 0 564 804 | 10/1993 |
| EP | 0 596 717 | 5/1994 |
| EP | 0 721 742 | 7/1996 |
| EP | 1 604 670 A1 | 12/2005 |
| JP | 2003-503080 A | 1/2003 |
| JP | 2004-091485 | 3/2004 |

(Continued)

OTHER PUBLICATIONS

Helmenstine, Anne Marie. What are Lipids: Definitions and Examples. ThoughtCo. (Year: 2018).*

(Continued)

*Primary Examiner* — Nghi V Nguyen
(74) *Attorney, Agent, or Firm* — Morgan, Lewis & Bockius LLP

(57) ABSTRACT

Provided is a composition for improving the nutritional status, reducing the frequency of fever, and/or increasing the immunocompetence of the elderly. The composition is one for improving the nutritional status, reducing the frequency of fever, and/or increasing the immunocompetence of the elderly and comprises the following components (a) to (e): (a) an antioxidant agent; (b) at least one component selected from the group consisting of vitamin $B_1$, vitamin $B_2$, vitamin $B_6$, niacin, and pantothenic acid; (c) at least one component selected from the group consisting of folic acid and vitamin $B_{12}$; (d) zinc; and (e) selenium.

17 Claims, 12 Drawing Sheets

(56) References Cited

FOREIGN PATENT DOCUMENTS

| JP | 2005-013134 | 1/2005 |
|---|---|---|
| JP | 2007-297346 | 11/2007 |
| WO | 99-58000 | 11/1999 |
| WO | 01/001789 A1 | 1/2001 |
| WO | 02-39834 | 5/2002 |
| WO | 02-47493 | 6/2002 |
| WO | 2003002148 A1 | 1/2013 |

OTHER PUBLICATIONS

Chinese language office action dated Jun. 30, 2011 and its English language translation for corresponding Chinese application 200980101837.2 cites the foreign patent document above.

An extended European search report for a counterpart application. Japanese Office Action dated Jul. 23, 2013 for corresponding Japanese Patent App. No. 2009-548911.
English translation of "Reason for Rejection" for Japanese Office Action dated Jul. 23, 2013 for corresponding Japanese Patent App. 2009-54891.
Observations by third party concerning the patentability of the invention dated Sep. 15, 2015 in the corresponding European patent application No. 09700459.2.
Wikipedia-Fever (2015).
Meydani SN "Vitamin/mineral supplementation, the aging immune response, and risk of infection", in Nutrition Reviews, Apr. 1993; vol. 51, No. 4, p. 106-109.
Summons to attend oral proceedings dated Oct. 12, 2017 in the corresponding European patent application No. 09700459.2.

\* cited by examiner

COMPOSITION FOR IMPROVING NUTRITIONAL STATUS, REDUCING FREQUENCY OF FEVER AND/OR INCREASING IMMUNOCOMPETENCE OF THE ELDERLY

CROSS REFERENCE TO RELATED APPLICATIONS

This application is a national stage of international application no. PCT/JP2009/050018, filed on Jan. 6, 2009, and claims priority under 35 USC 119 to Japanese application no. 2008-003072, filed on Jan. 10, 2008, which are incorporated herein by reference.

TECHNICAL FIELD

The present invention relates to a composition for improving the nutritional status, reducing the frequency of fever, and/or increasing the immunocompetence of the elderly.

BACKGROUND ART

The elderly are prone to chronic malnutrition due to a decrease in basic energy intake, reduced metabolism, an underlying disease, and the like. Even when the elderly take in sufficient energy and are given sufficient amounts of the three major nutrients and the like, they often cannot efficiently metabolize the nutrients taken in because their energy metabolic capacity has decreased. In malnutrition or a catabolic state, immunocompetence is reduced due to lowered immune cell synthesis caused by marked exhaustion or a deficiency in various nutrients, and susceptibility to infection is increased. Administration of vitamins which contribute to efficient metabolism of the three major nutrients and micronutrients involved in protein synthesis is important for improving the nutritional status and increasing the immunocompetence of the elderly and reducing their susceptibility to infection (Non-Patent document 1).
Non-Patent Document 1: FUTAMURA, Akihiko et al., Journal of Medical Technology, Vol. 48, No. 9, 2004, 3. Evaluation of Immunocompetence

DISCLOSURE OF THE INVENTION

Problem to be Solved by the Invention

An object of the present invention is to provide a composition for improving the nutritional status, reducing the frequency of fever, and/or increasing the immunocompetence of the elderly.

Means for Solving the Problem

The present inventors asked inpatients at the age of 65 and older to take a composition containing the following components (a) to (e) in order to verify the usefulness of the composition. As a result, the inventors have found that the composition is effective in improving the nutritional status, reducing the frequency of fever, and/or increasing the immunocompetence of the elderly, thereby completing the present invention:
(a) an antioxidant agent;
(b) at least one component selected from the group consisting of vitamin $B_1$, vitamin $B_2$, vitamin $B_6$, niacin, and pantothenic acid;
(c) at least one component selected from the group consisting of folic acid and vitamin $B_{12}$;
(d) zinc; and
(e) selenium.

The present invention is summarized as follows.
(1) A composition for improving the nutritional status, reducing the frequency of fever, and/or increasing the immunocompetence of the elderly, comprising the following components (a) to (e):
(a) an antioxidant agent;
(b) at least one component selected from the group consisting of vitamin $B_1$, vitamin $B_2$, vitamin $B_6$, niacin, and pantothenic acid;
(c) at least one component selected from the group consisting of folic acid and vitamin $B_{12}$;
(d) zinc; and
(e) selenium.
(2) The composition according to (1), wherein the antioxidant agent is an antioxidant vitamin.
(3) The composition according to (2), wherein the antioxidant vitamin is at least one member selected from the group consisting of vitamin C, vitamin E, and β-carotene.
(4) The composition according to any of (1) to (3), further comprising vitamin $D_3$ and/or iron.
(5) The composition according to (4), comprising vitamin C, vitamin E, β-carotene, vitamin $B_1$, vitamin $B_2$, vitamin $B_6$, niacin, pantothenic acid, folic acid, vitamin $B_{12}$, zinc, selenium, vitamin $D_3$, and iron.
(6) The composition according to (5), comprising, per dosage unit, 350±70 mg of vitamin C, 14±2.8 mg of vitamin E, 4.6±0.92 mg of β-carotene, 2.1±0.42 mg of vitamin $B_1$, 2.1±0.42 mg of vitamin $B_2$, 3.5±0.7 mg of vitamin $B_6$, 10.5±2.1 mg of niacin, 7.0±1.4 mg of pantothenic acid, 560±112 μg of folic acid, 7.0±1.4 μg of vitamin $B_{12}$, 7.0±1.4 mg of zinc, 35±7 μg of selenium, 2.6±0.52 μg of vitamin $D_3$, and 3.5±0.7 mg of iron, and having an energy of 47±9.4 kcal.
(7) The composition according to any of (1) to (6), further comprising galacto-oligosaccharide, potassium, calcium, magnesium, and phosphorus.
(8) The composition according to (7), comprising, per dosage unit, 1.1±0.22 g of galacto-oligosaccharide, 41±8.2 mg of potassium, 41±8.2 mg of calcium, 2.2±0.44 mg of magnesium, and 11±2.2 mg of phosphorus.
(9) The composition according to any of (1) to (8) using fruit juice and/or vegetable juice as a base.
(10) The composition according to any of (1) to (9) forming a gel.
(11) The composition according to (10), wherein a gelatinizing agent used is one or more polysaccharide thickeners.
(12) The composition according to (11) having a gel strength of 7,000±2,000 $N/m^2$ at 5° C.
(13) The composition according to (12), wherein, when the gel strength is 7,000±2,000 $N/m^2$, adhesion energy is 60±40 $J/m^3$ and cohesiveness is 0.7±0.1 $J/m^3$.
(14) The composition according to any of (1) to (13) having a volume of 70±14 mL per dosage unit.
(15) A method for improving the nutritional status, reducing the frequency of fever, and/or increasing the immunocompetence of the elderly, comprising administering to a subject the following components (a) to (e) in amounts effective for improving the nutritional status, reducing the frequency of fever, and/or increasing the immunocompetence of the elderly:

(a) an antioxidant agent;
(b) at least one component selected from the group consisting of vitamin $B_1$, vitamin $B_2$, vitamin $B_6$, niacin, and pantothenic acid;
(c) at least one component selected from the group consisting of folic acid and vitamin $B_{12}$;
(d) zinc; and
(e) selenium.

(16) Use of the following components (a) to (e) for production of a composition for improving the nutritional status, reducing the frequency of fever, and/or increasing the immunocompetence of the elderly:
(a) an antioxidant agent;
(b) at least one component selected from the group consisting of vitamin $B_1$, vitamin $B_2$, vitamin $B_6$, niacin, and pantothenic acid;
(c) at least one component selected from the group consisting of folic acid and vitamin $B_{12}$;
(d) zinc; and
(e) selenium.

(17) A composition to be used for improving the nutritional status, reducing the frequency of fever, and/or increasing the immunocompetence of the elderly, comprising the following components (a) to (e):
(a) an antioxidant agent;
(b) at least one component selected from the group consisting of vitamin $B_1$, vitamin $B_2$, vitamin $B_6$, niacin, and pantothenic acid;
(c) at least one component selected from the group consisting of folic acid and vitamin $B_{12}$;
(d) zinc; and
(e) selenium.

Advantage of the Invention

According to the composition of the present invention, an improvement in nutritional status, a reduction in frequency of fever, and/or an increase in immunocompetence of the elderly are possible.

The present specification encompasses the description set forth in the specification and/or drawings of Japanese Patent Application No. 2000-003072, based on which the present application claims priority.

BEST MODE FOR CARRYING OUT THE INVENTION

Figure 1:
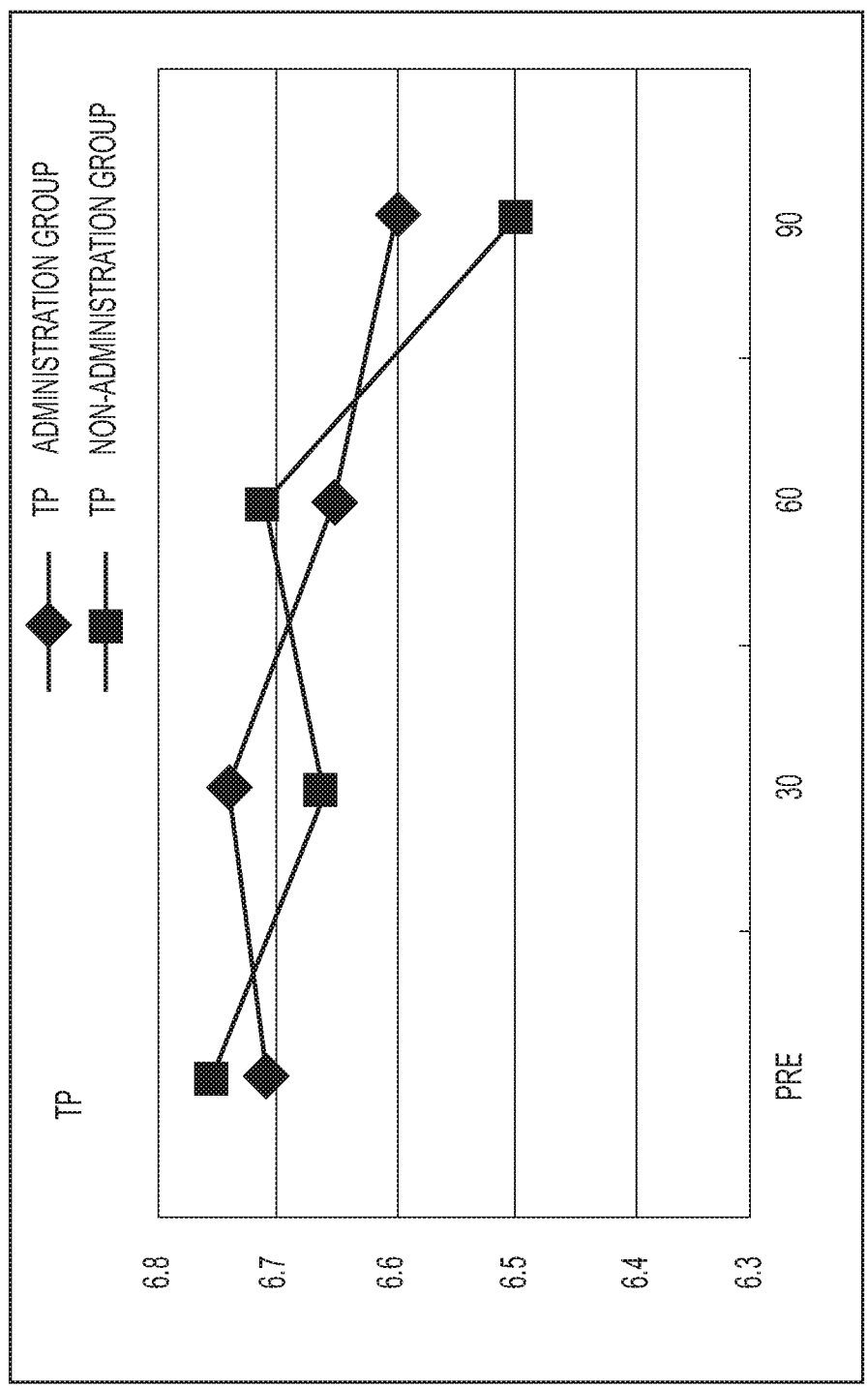
FIG. 1 shows the results of measurement of the total protein (TP). A diamond ♦ represents the administration group, and a square ■ represents the non-administration group. Measurement values were averaged out for each group and the values thus obtained were graphed. The vertical axis represents the serum total protein concentration (g/dl), and the horizontal axis represents the number of days elapsed. A standard total protein level is 6.5 to 8.2 g/dl. Although a decreasing tendency was exhibited in both groups, no significant difference was observed in comparison with the baseline.

Hereinafter, embodiments of the present invention will be described in more detail.

The present invention provides a composition for improving the nutritional status, reducing the frequency of fever, and/or increasing the immunocompetence of the elderly, comprising the following components (a) to (e):

(a) an antioxidant agent;
(b) at least one component selected from the group consisting of vitamin $B_1$, vitamin $B_2$/vitamin $B_6$, niacin, and pantothenic acid;
(c) at least one component selected from the group consisting of folic acid and vitamin $B_{12}$;
(d) zinc; and
(e) selenium.

As described above, a composition containing vitamins, zinc, and the like induces a biological function, for example, it induces promotion of metabolism, protein synthesis, synthesis of a lymphocyte such as a T-cell, and activation of cell growth, and reinforces an antioxidant action and the like, whereby the nutritional status of the elderly is improved, and therefore the frequency of fever can be reduced and/or their immunocompetence can be increased.

The components in the composition of the present invention are broadly classified into an antioxidant agent, a metabolic cofactor, and a cell growth-promoting factor.

An antioxidant agent has a strong reducing action on oxidative stress associated with a disease and aging. Examples of the antioxidant agent as described above include antioxidant vitamins such as vitamin C, vitamin E, and β-carotene. Because these antioxidant vitamins act at different stages, it is preferable to use them simultaneously, rather than using any of them alone. Also, vitamin C, which is one of the above-described antioxidant vitamins, not only functions as an antioxidant agent but is directly involved in enhancement of cAMP and solubilization of lipid, and has various actions such as collagen formation, detoxification of a foreign substance in a living body, induction of interferon production, an anti-histamine action, enhancement of immune function, an antiviral action, and an antibacterial action. Therefore, it is preferable to incorporate at least vitamin C as an antioxidant vitamin.

When an antioxidant vitamin is used as an antioxidant agent, the amount to be added to the composition is, in terms of the content per dosage unit, appropriately in the range of 100 to 2000 mg, preferably 300 to 1000 mg in the case of vitamin C, appropriately in the range of 3.0 to 600 mg, preferably 5.0 to 300 mg in the case of vitamin E, and appropriately in the range of 2.0 to 10.0 mg, preferably 4.0 to 7.0 mg in the case of β-carotene.

It is to be noted that although the above-described antioxidant vitamin agents have been shown as preferable embodiments of the above-described antioxidant agents, the antioxidant agents are not limited to the antioxidant vitamin agents, and an antioxidant substance contained in food and the like such as polyphenol and catechin can be used instead of or as supplements to the above-described antioxidant vitamin agents. Further, selenium is a constitutive substance of glutathione peroxidase which is an antioxidant enzyme, and zinc is a constitutive substance of superoxide dismutase which is another antioxidant enzyme.

As a metabolic cofactor contained in the composition of the present invention, any or all of vitamin $B_1$, vitamin $B_2$, vitamin $B_6$, vitamin $B_{12}$, niacin, pantothenic acid, and folic acid can be added. These vitamins that assist in metabolism have a role as a coenzyme associated with the metabolism of saccharides, lipids, and amino acids, and are important components for the vital activity of life. For example, vitamin $B_1$ is involved in regulation of glycolysis, TCA cycle, and β-oxidation as thiamine pyrophosphate (TPP) and vitamin $B_2$ is involved in the above-described regulation as flavin mononucleotide (FMN) and flavin-adenine dinucleotide (FAD). Vitamin $B_6$ is involved in amino acid metabolism as pyridoxal phosphate and the like. Niacin is involved in glycolysis and lipid metabolism as NAD and NADP. Also, pantothenic acid is involved in TCA cycle, amino acid metabolism, and lipid metabolism as CoA. Folic acid participates in amino acid metabolism and nucleic acid metabolism as FH4. Vitamin $B_{12}$ is involved in amino acid metabolism as CoB12.

Accordingly, these vitamins are components that constitute different coenzymes, so it is preferable to use all of these vitamins as the above-described metabolic cofactor. Particularly, the intake amount of these vitamins varies depending on the amounts of energy and protein in taken, and the intake amount of these vitamins tends to be generally insufficient in the elderly who take in only small amounts of food and the elderly who suffer reduced absorption rates or utilization rates are. Therefore, in order to ensure that an intracellular energy supply as required in the elderly is efficiently carried out, it is preferable to add all members of the above-described group of vitamins into the composition.

The amount of the above-described vitamins to be added to the composition is, in terms of the content per dosage unit, appropriately in the range of 0.5 to 10 mg, preferably 1.0 to 5.0 mg in the case of vitamin $B_1$, appropriately in the range of 0.5 to 20 mg, preferably 1.0 to 10 mg in the case of vitamin $B_2$, appropriately in the range of 1.6 to 60 mg, preferably 3.0 to 8.0 mg in the case of vitamin $B_6$, appropriately in the range of 1.1 to 50.0 µg, preferably 5.0 to 15.0 µg in the case of vitamin $B_{12}$, appropriately in the range of 1.0 to 100 mg, preferably 5.0 to 50 mg in the case of niacin, appropriately in the range of 200 µg to 1.1 mg, preferably 500 to 1,000 µg in the case of folic acid, and appropriately in the range of 1.0 to 100 mg, preferably 5.0 to 50 mg in the case of pantothenic acid.

Further, a cell growth-promoting factor to be contained in the composition of the present invention is a factor capable of promoting cell differentiation and proliferation. As the cell growth-promoting factor, folic acid, vitamin $B_{12}$, β-carotene, zinc, and the like may be mentioned as examples, and any or all of these can be used Folic acid and vitamin $B_{12}$ mentioned above not only function as metabolic cofactors in a living body but also have a function to promote cell differentiation and proliferation. Also, β-carotene has a function to promote cell differentiation and proliferation, besides its function as an antioxidant vitamin. Since promoting cell proliferation and differentiation also enables promoted proliferation of an immune cell such as a T-cell which is one of the lymphocytes, immunocompetence can be increased, and as result, a capacity to heal wounds and the like and defense against an infection can be strengthened.

The amount of each component to be added to the composition is, in terms of the content per dosage unit, as described above with respect to folic acid, vitamin $B_{12}$ and β-carotene, while the amount of zinc to be added is appropriately 1.2 to 30 mg, preferably 9.0 to 12 mg.

Further, zinc can also be used as a cofactor for nucleic acid and protein syntheses. Zinc is bound to albumin, globulin, and the like in a living body and circulates throughout the body, reaching every part of it. It is known that, in hypozincemia, zinc is mobilized from epithelial cells in the skin, the gastrointestinal tract, and the like, and from the bone, and the like into the liver, readily causing zinc deficiency in these epithelial tissues. It is preferable to add a cofactor for nucleic acid and protein syntheses, for example, zinc, in order to improve the nutritional status of the elderly. Also, when zinc is used, it is preferable to use a zinc component produced by yeast (zinc yeast), which is approved as a food additive and has high bioavailability.

As described above, the constitutive components of the present composition are an antioxidant agent, a metabolic cofactor, and a cell growth-promoting factor. Because one of these components may have duplicative actions, there is no need to use different substances as the respective constitutive elements, and one substance may be used as a plurality of constitutive elements.

Furthermore, other additional substances can be supplemented besides the above-described constitutive elements. For example, considering that iron deficiency and the like develop in the elderly who take in only small amounts of food, addition of iron to the composition is also possible. Also, calcium, as well as vitamin D which promotes calcium absorption (for example, vitamin $D_3$), and the like can be added. The amount to be added to the composition of the present invention is, in terms of the content per dosage unit, appropriately in the range of 0.5 to 50 mg, preferably 1.0 to 30 mg in the case of iron, and appropriately in the range of 1.0 to 10 µg, preferably 2.0 to 8.0 µg in the case of vitamin $D_3$.

Furthermore, an intestinal regulation substance, for example, raffinose, can be added.

Besides the above, vitamin A, biotin, chromium, coenzyme Q, α-lipoic acid, and the like can be added. Vitamin A has a function to promote cell differentiation and proliferation, besides its function as an antioxidant vitamin. Since promoting cell proliferation and differentiation can also promote proliferation of an immune cell such as a T-cell, immunocompetence can be increased, and therefore defense against an infection can be strengthened. Biotin is a coenzyme having a fatty acid metabolism action, and skin inflammation and hair loss may be caused when biotin is deficient. Chromium increases insulin sensitivity by enhancing the insulin receptor binding capacity increasing the number of insulin receptors, and enhancing insulin receptor kinase activity. As coenzyme Q10 has a strong antioxidative action, it is anticipated to exhibit prophylactic and preventive effects on diseases attributable to oxidative stress. Also, because coenzyme Q10 is a component involved in ATP production, an effect for smooth metabolism of nutrients is anticipated by supplementation of coenzyme Q10. The α-lipoic acid is involved in promotion of a glucose metabolism. It is considered that α-lipoic acid stimulates mobilization of an intracellular glucose transporter (GLUT-4) to a cellular membrane, whereby the amount of glucose uptake mediated by insulin in muscle and a myocyte is considerably increased.

A preferred embodiment of the present invention is a composition containing vitamin C, vitamin E, β-carotene, vitamin $B_1$, vitamin $B_2$, vitamin $B_6$, niacin, pantothenic acid, folic acid, vitamin $B_{12}$, zinc, selenium, vitamin $D_3$, and iron. A more preferred embodiment of the present invention is a composition containing, per dosage unit, 350±70 mg of vitamin C, 14±2.8 mg of vitamin E, 4.6±0.92 mg of β-carotene, 2.1±0.42 mg of vitamin $B_1$, 2.1±0.42 mg of vitamin $B_2$, 3.5±0.7 mg of vitamin $B_6$, 10.5±2.1 mg of niacin, 7.0±1.4 mg of pantothenic acid, 560±112 µg of folic acid, 7.0±1.4 µg of vitamin $B_{12}$, 7.0±1.4 mg of zinc, 35±7 µg of selenium, 2.6±0.52 µg of vitamin $D_3$, and 3.5±0.7 mg of iron, and having an energy of 47±9.4 kcal.

The composition of the present invention can further contain other components besides the above-described components. For example, the composition of the present invention can contain galacto-oligosaccharide, potassium, calcium, magnesium, phosphorus, and the like. Deficiency of a certain component in a restricted diet such as nursing food and swallowing-training food can be prevented by incorporating the above-described components in the composition of the present invention.

The content of galacto-oligosaccharide, for example, in the composition of the present invention is, per dosage unit, appropriately 0.1 to 20 g, preferably 1.0 to 10 g, the content of potassium is appropriately 10 to 1,000 mg, preferably 15 to 500 mg, the content of calcium is appropriately 1.0 to 2,300 mg, preferably 10 to 600 mg, the content of magnesium is appropriately 0.1 to 10 mg, preferably 1.0 to 5.0 mg, and the content of phosphorus is appropriately 1.0 to 3,500 mg, preferably 5.0 to 1,000 mg.

A preferred embodiment of the present invention is a composition containing, per dosage unit, 1.1±0.22 g of galacto-oligosaccharide, 41±8.2 mg of potassium, 41±8.2 mg of calcium, 2.2±0.44 mg of magnesium, and 11±2.2 mg of phosphorus.

The above-described components are mixed and the composition of the present invention can be prepared into such dosage forms as powder, granule, tablet, and liquid. The composition of the present invention is preferably provided as a gelled product so that the elderly can easily take in the Composition. When the composition is provided as a gelled product, those aged persons who are capable of oral ingestion can take in the composition orally.

When the composition of the present invention is to be provided as a gelled product, a gelatinizing agent may be dissolved in water, and after incorporating each component of the composition, the resulting mixture may be placed in a container and cooled. As needed, heat may be applied to dissolve the gelatinizing agent in water, or the container may be sealed, or the composition may be subjected to heat sterilization. For oral administration, fruit juice, vegetable juice, and the like may be used instead of water in order to improve taste. The amount of water, fruit juice, or vegetable juice to be added to the composition of the present invention is appropriately 5.0 to 50.0 g, preferably 10.0 to 20.0 g, more preferably 15.0±0.3 g, as the content per dosage unit. Examples of the fruit juice and vegetable juice include blueberry juice, grape juice, grapefruit juice, lemon juice, orange juice, carrot juice, apple juice, pineapple juice, and peach juice. Among them, carrot juice, blueberry juice, and grape juice are preferable for the reason that the sourness and smell of vitamin C and a group of B vitamins can be relieved. In the case of a gelled product, the volume is appropriately 25 to 200 ml, preferably 50 to 100 ml, and more preferably 70±14 ml, per dosage unit. Also, in the case of a gelled product, the water content may be, for example, approximately 61±12.2 g per dosage unit.

Examples of the gelatinizing agent that can be used include, polysaccharide thickeners such as dextrin, agar, xanthan gum, locust bean gum, carrageenan, and pectin, as well as gellan gum, psyllium seed gum, tara gum, guar gum, glucomannan, alginic acid, tamarind seed gum, cellulose, and the like. It is preferable to use one or more polysaccharide thickeners. The amount of the gelatinizing agent to be added to the composition of the present invention is appropriately 0.5 to 2.0 g, preferably 0.75 to 1.0 g, and more preferably 0.82±0.16 g, as the content per dosage unit.

Although the gel strength of the gelled product is not particularly limited as long as the elderly can consume the product, it is preferably 7,000±2,000 N/m² at 5° C.

Also, it is preferable that adhesion energy be 60±40 J/m³ and cohesiveness be 0.7±0.1 J/m³, when the gel strength is 7,000±2,000 N/m². The gel having low adhesiveness and high cohesiveness as described above is most suitable for swallowing.

The gel strength can be measured as follows. Using a gel strength measurement instrument consisting of a Yamaden texturometer and a plunger with a diameter of 16 mm, measurement is conducted at a measurement temperature of 25° C., compression speed (speed at which the plunger is pushed down) of 10 mm/s, a measurement strain rate (indentation rate with respect to the thickness of a sample) of 40.00%, and a distance of 10.00 mm, by which the plunger is pushed down, with two pushings of the plunger.

In the above-described gel strength measurement, the adhesion energy is measured as a negative energy observed as the plunger is pulled up after it has been pushed down once.

In the above-described gel strength measurement, the cohesiveness is measured as the ratio between the energy observed in the first pushing of the plunger and the energy observed in the second pushing.

The amount of energy in the composition of the present invention is appropriately 10 to 200 kcal, preferably 20 to 100 kcal, per dosage unit. Also, with regard to general components, the content of protein, for example, may be approximately 0.7±0.14 g, the content of carbohydrate may be approximately 10.5±2.1 g, the content of dietary fiber may be approximately 0.7±0.14 g, the content of sodium may be approximately 16.8±3.36 mg, and the content of water may be approximately 61±12.2 g, per dosage unit.

An example of a standard table for components in the composition of the present invention (in 70 mL±14 mL) is shown in Table 1 below.

TABLE 1

| | | |
|---|---|---|
| Energy | | 47 ± 9.4 kcal |
| General components | Protein | 0.7 ± 0.14 g |
| | Lipid | 0 g |
| | Carbohydrate | 10.5 ± 2.1 g |
| | Dietary fiber | 0.7 ± 0.14 g |
| | Sodium | 16.8 ± 3.36 mg |
| Minerals | Potassium | 41 ± 8.2 mg |
| | Calcium | 41 ± 8.2 mg |
| | Magnesium | 2.2 ± 0.44 mg |
| | Phosphorus | 11 ± 2.2 mg |
| Trace elements | Iron | 3.5 ± 0.7 mg |
| | Zinc | 7 ± 1.4 mg |
| | Copper | 0.01 ± 0.002 mg |
| | Selenium | 35 ± 7 μg |
| Vitamins | β-carotene | 4.6 ± 0.92 mg |
| | Vitamin $B_1$ | 2.1 ± 0.42 mg |
| | Vitamin $B_2$ | 2.1 ± 0.42 mg |
| | Vitamin $B_6$ | 3.5 ± 0.7 mg |
| | Vitamin $B_{12}$ | 7 ± 1.4 μg |
| | Vitamin C | 350 ± 70 mg |
| | Niacin | 10.5 ± 2.1 mg |
| | Folic acid | 560 ± 112 μg |
| | Vitamin $D_3$ | 2.6 ± 0.52 μg |
| | Vitamin E | 14 ± 2.8 mg |
| | Pantothenic acid | 7 ± 1.4 mg |
| Galacto-oligosaccharide | | 1.1 ± 0.22 g |
| Water | | 61 ± 12.2 g |

Raw materials include glucose, fermented milk, galacto-oligosaccharide, carrot juice, powdered skim milk, zinc yeast, selenium yeast, a gelatinizing agent (a polysaccharide thickener), vitamin C, a seasoning (an amino acid), calcium lactate, a flavor, an acidulant, vitamin E, β-carotene, sodium ferric citrate, acesulfame potassium, niacin, pantothenic acid, vitamin $B_6$, vitamin $B_2$, vitamin $B_1$, vitamin D, folic acid, vitamin $B_{12}$, gelatin, and the like.

An improving effect on the nutritional status, reducing effect on the frequency of fever, and/or an increasing effect on the immunocompetence of the elderly, the effects exhibited by the composition prepared as above, can be confirmed by measuring examination items such as total protein, albumin, prealbumin, red blood cell count, white blood cell count, platelet count, hemoglobin, hematocrit, total lymphocyte count, neutrophil count, and C-reactive protein, as well as the frequency of fever, both before and after administration of the composition to the elderly, and then observing any differences between values measured before and after administration. Alternatively, a value measured in a group to which the composition has been administered and a value measured in a group to which a placebo (for example, a commercially available jelly) has been administered (control group) can be compared.

A standard level of each of the above substances in the blood is as follows; total protein, 6.5 to 8.2 g/dl; albumin, 3.5 to 5.0 g/dl; prealbumin, 10 to 40 mg/dl; red blood cell count, 4.4 million to 5.4 million/mm3 (male) and 3.8 million to 4.6 million/mm3 (female); white blood cell count, 4000 to 8000/μl; platelet count, 130 thousand to 400 thousand/μl; hemoglobin, 13.0 to 16.6 g/dl (male) and 11.4 to 14.6 g/dl (female); hematocrit, 38.0 to 48.9% (male) and 34.0 to 43.9% (female); total lymphocyte count, 1500 to 4000/μl; and neutrophil count, 1830 to 7250/μl. If, as a result of an examination of the elderly administered with the composition of the present invention, measured values in the above-described examination items are found to be within the ranges of the standard levels shown above, it can be said that nutritional status has been improved or immunocompetence improved in the elderly.

As described above, the composition of the present invention can be used for improving the nutritional status, reducing the frequency of fever, and/or increasing the immunocompetence of the elderly. The composition of the present invention may be is advantageously administered to the elderly in a dose of one dosage unit per day. The composition of the present invention is advantageously administered orally.

EXAMPLES

Hereinafter, the present invention is specifically described with Examples. It is to be noted that the Examples are provided to illustrate the present invention, not to limit the scope of the present invention.

[Preparation Example 1] Preparation of the Composition

A method for adjusting a mixture having a volume of 300 L is described. To 220 L of water, 12.3 kg of galacto-oligosaccharide was dissolved, after which 1.1 kg of pectin, 3.6 kg of gelatinizing agent, 1.6 kg of powdered skim milk, and 40.0 kg of glucose were dissolved. While stirring, the temperature was raised to 80° C., and the resulting solution was mixed with a separately prepared solution of 0.64 kg of zinc yeast, 0.16 kg of selenium yeast, 4.05 kg of vitamin mix (an admixture containing 22.9 g of β-carotene, 1718.7 g of vitamin C, 9.7 g of vitamin B1, 14.5 g of vitamin B2, 16.9 g of vitamin B6, 0.061 g of vitamin B12, 49.1 g of niacin, 3.1 g of folic acid, 0.012 g of vitamin D, 70.7 g of vitamin E, and 42.2 g of pantothenic acid), 0.26 kg of vitamin C, 0.066 kg of acesulfame potassium, 1.16 kg of calcium lactate, 0.162 kg of sodium ferric citrate, and 10.9 kg of concentrated carrot juice. Further, 32.4 kg of lactobacillus drink and 0.64 kg of a flavor were added to the resulting mixture, after which the mixture was placed in containers each having a volume of 70 mL. The solution was then subjected to boiling sterilization, and then cooled. The composition had the following properties; a gel strength of $7,000 \pm 2,000$ N/m$^2$, an adhesion energy of $60 \pm 40$ J/m$^3$, and a cohesiveness of $0.7 \pm 0.1$ J/m$^3$, at 5° C.

[Example 1] Usefulness of the Composition

1. Objective

To verify if administration of the composition prepared in Preparation Example 1 to the elderly would increase energy efficiency to enable inhibition of protein catabolism, an increase in protein in the blood, and inhibition of frequency of fever.

2. Method

Subjects were inpatients who were at the age of 65 or older. The subjects were assigned to an administration group and a group in which the composition would not be administered (hereinafter, a non-administration group), and the administration group consumed one serving of the above-described composition (70 mL) in addition to regular lunch, while the non-administration group consumed only a regular diet. The administration period was 90 days, and the blood was collected before administration and at day 30, day 60, and day 90 of administration for measurement of transthyretin (TTR), the total lymphocyte count (TLC), and the like. Further, the frequency of fever during the period was checked.

3. Results

Figure 2:
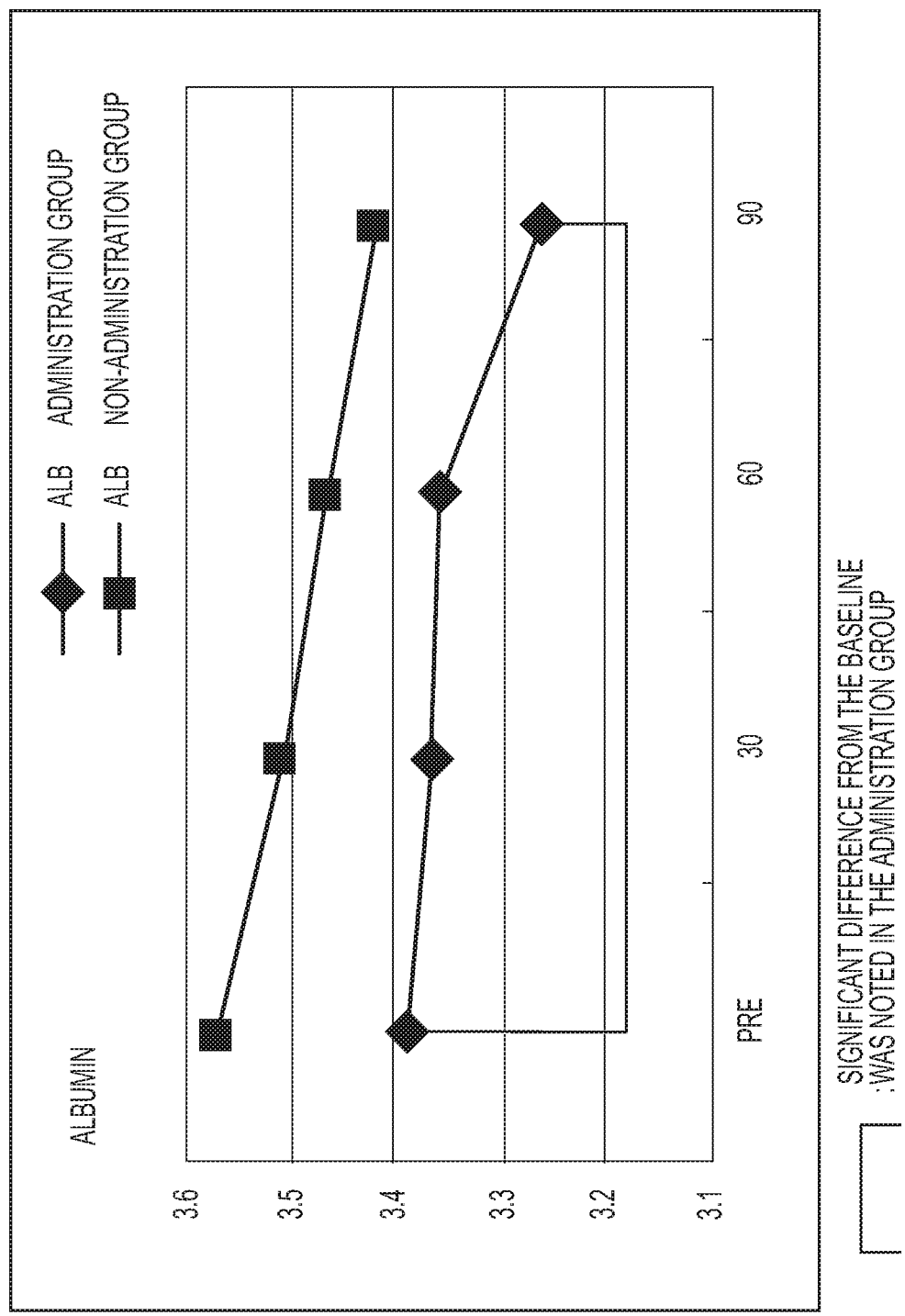
FIG. 2 shows the results of measurement of albumin (ALB). A diamond ♦ represents the administration group, and a square ■ represents the non-administration group. Measurement values were averaged out for each group and the values thus obtained were graphed. The vertical axis represents the serum albumin concentration (g/dl), and the horizontal axis represents the number of days elapsed. A standard albumin level is 3.7 to 5.3 g/dl. A decreasing tendency was exhibited in both groups, and a significant decrease ($p<0.05$) was observed in the administration group as compared with the baseline.
Figure 3:
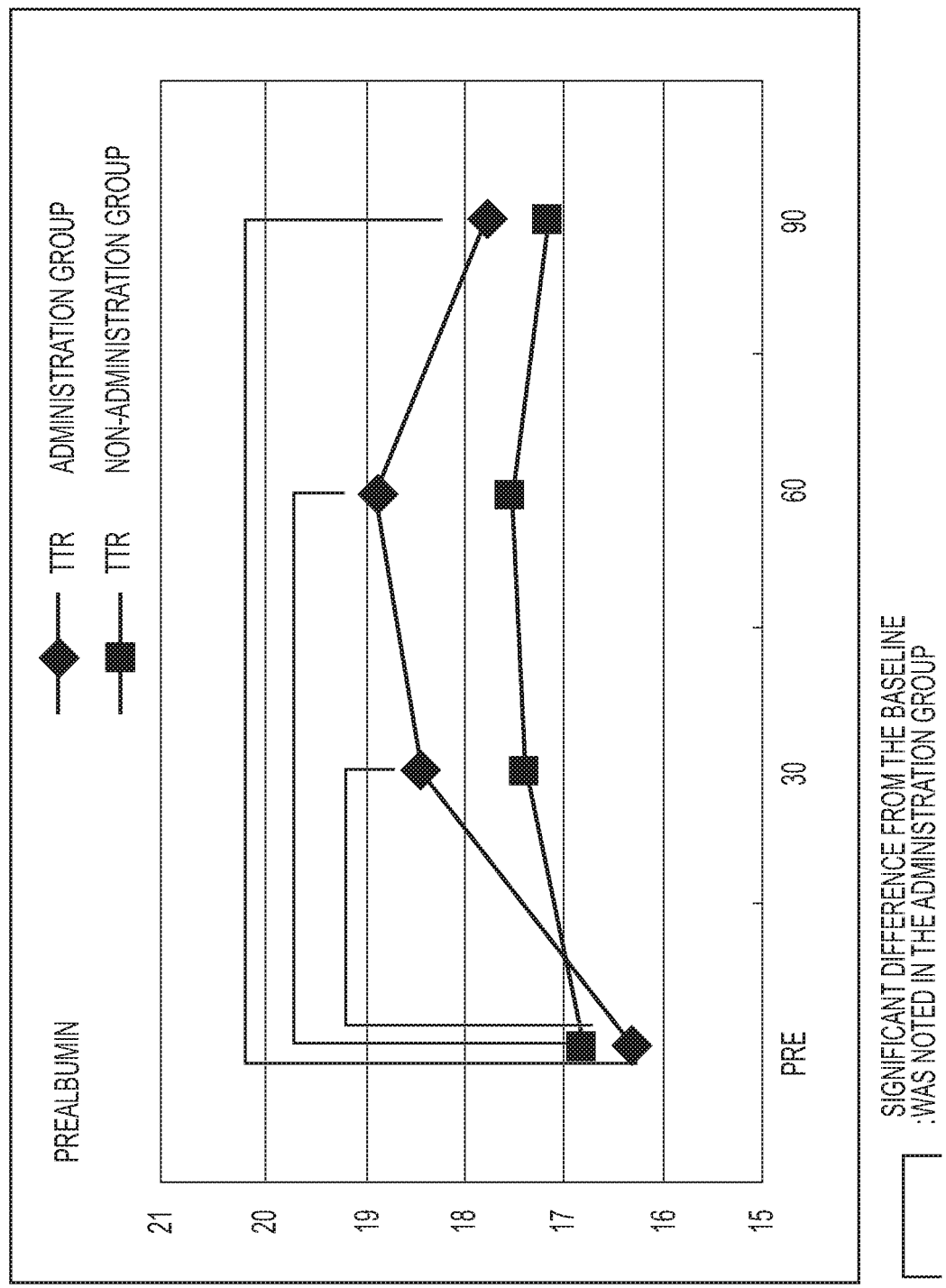
FIG. 3 shows the results of measurement of prealbumin (TTR). A diamond ♦ represents the administration group, and a square ■ represents the non-administration group. Measurement values were averaged out for each group and the values thus obtained were graphed. The vertical axis represents the prealbumin concentration (mg/dl), and the horizontal axis represents the number of days elapsed. A standard prealbumin level is 22 to 40 mg/dl. A significant increase ($p<0.05$) was observed after 30, 60, and even 90 days of administration in the administration group as compared with the baseline. On the other hand, no change was observed in the non-administration group.
Figure 4:
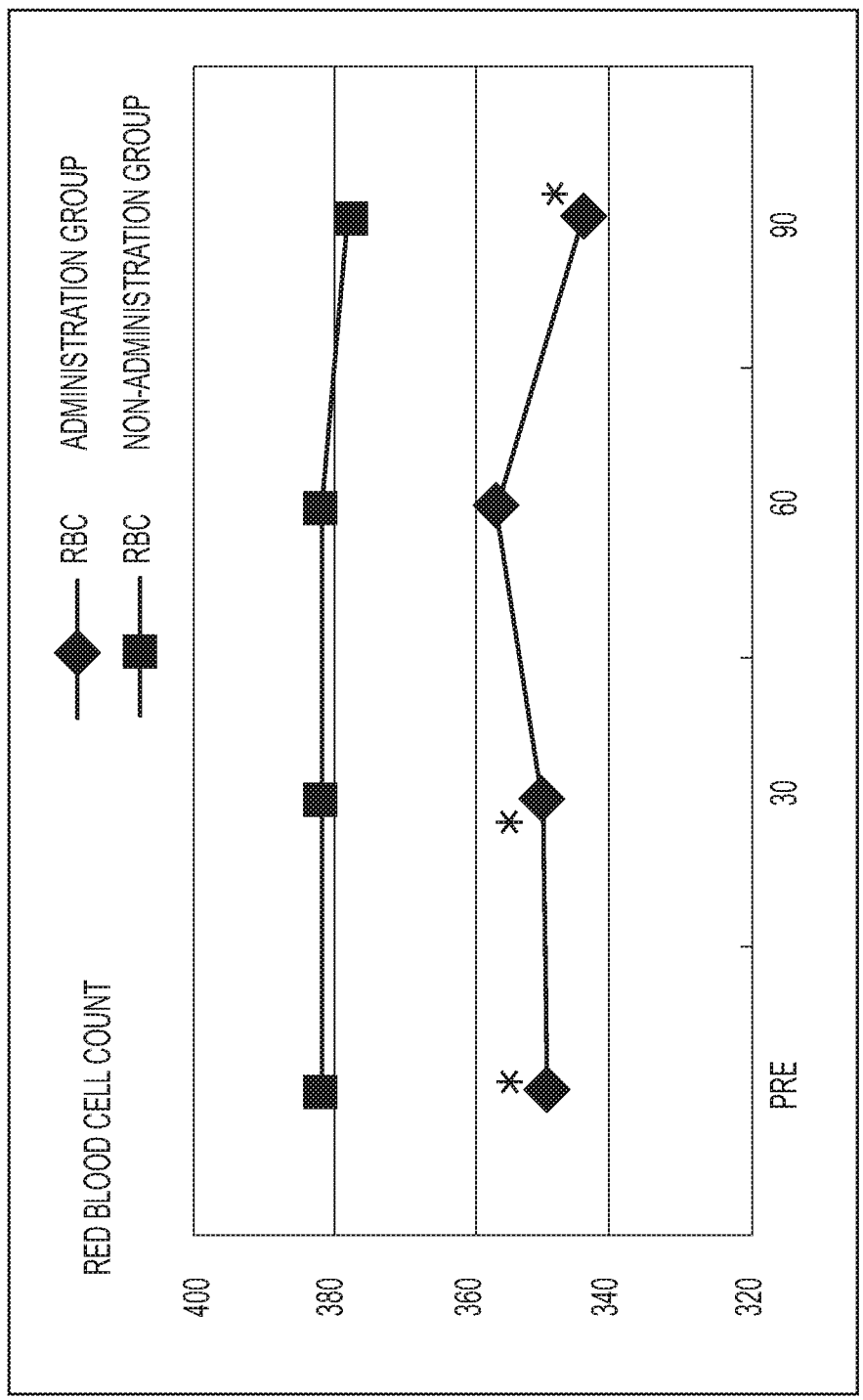
FIG. 4 shows the results of measurement of the red blood cell count (RBC). A diamond ♦ represents the administration group, and a square ■ represents the non-administration group. Measurement values were averaged out for each group and the values thus obtained were graphed. The vertical axis represents the red blood cell count (ten thousand/µl), and the horizontal axis represents the number of days elapsed. A standard red blood cell count is 4.2 million; to 5.7 million/µl for males (M), and 3.76 million to 5 million/µl for females (F). The RBC count was significantly lower ($p<0.05$) in the administration group as compared with the non-administration group. No change was observed in either group as compared with the baseline.
Figure 5:
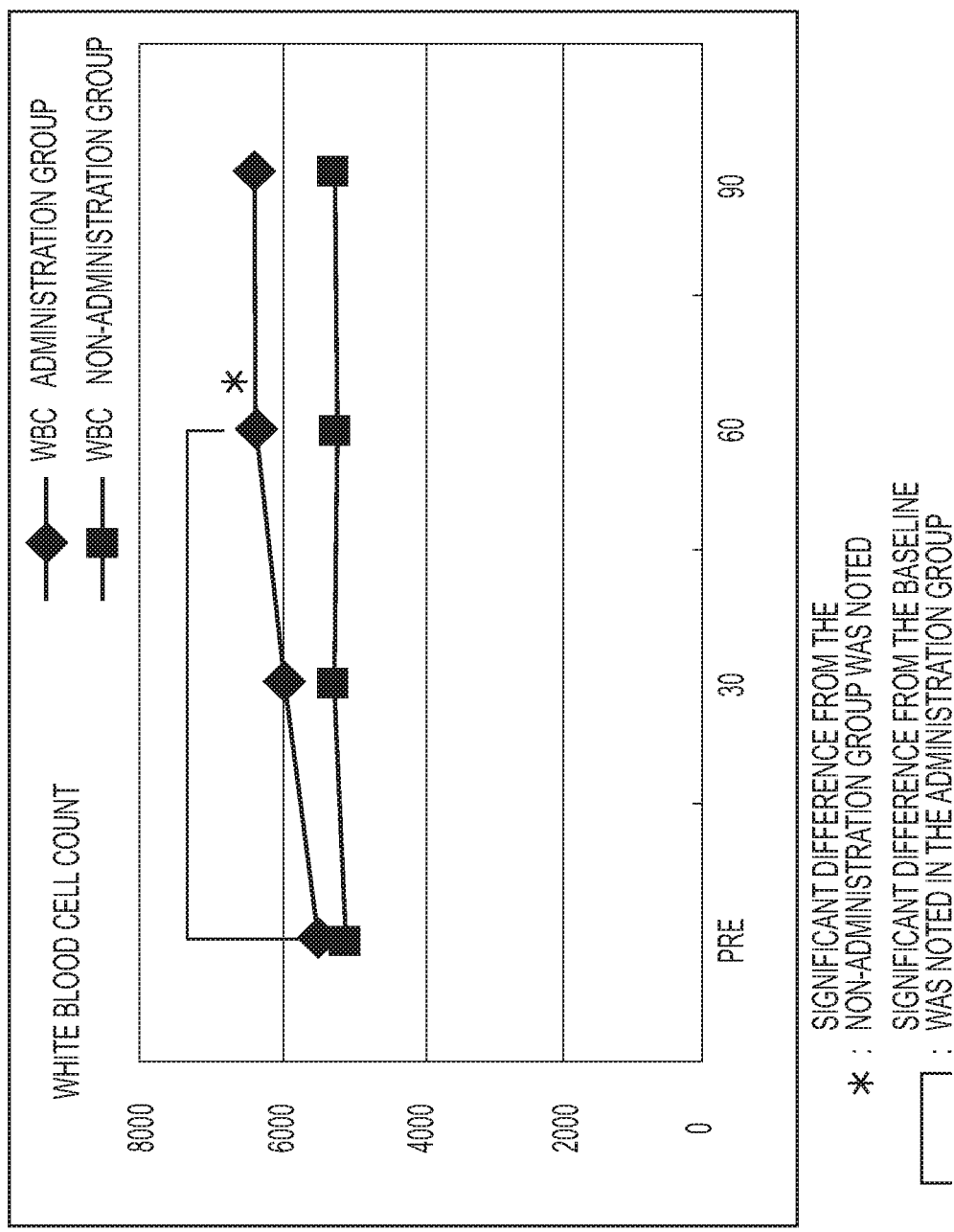
FIG. 5 shows the results of measurement of the white blood cell count (WBC). A diamond ♦ represents the administration group, and a square ■ represents the non-administration group. Measurement values were averaged out for each group and the values thus obtained were graphed. The vertical axis represents the white blood cell count (µl), and the horizontal axis represents the number of days elapsed. A standard white blood cell count is 3800 to 9800 µl for males (M), and 3500 to 9100 µl for females (F). The white blood cell count was significantly increased ($p<0.05$) in the administration group at day 60 of administration as compared with the baseline, and it was also significantly increased ($p<0.05$) with respect to the non-administration group.
Figure 6:
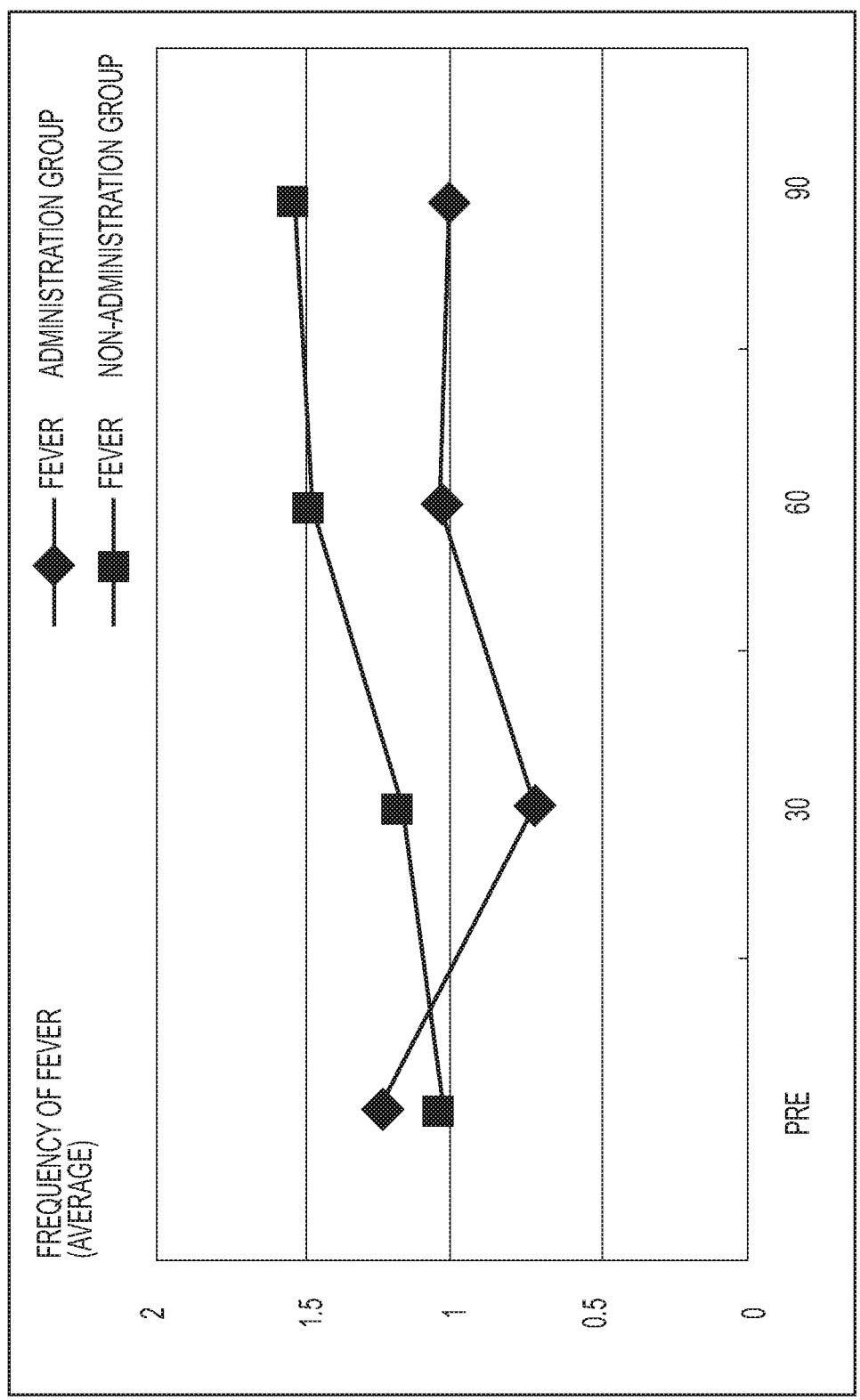
FIG. 6 shows the results of measurement of the frequency of fever. A diamond ♦ represents the administration group, and a square ■ represents the non-administration group. The frequency of fever was averaged out for each group and the values thus obtained were graphed. The vertical axis represents the average frequency of fever (the number of times), and the horizontal axis represents the number of days elapsed. While an increasing tendency was exhibited in the non-administration group ($1.1 \rightarrow 1.2 \rightarrow 1.5 \rightarrow 1.6$ times), a decreasing tendency was exhibited in the administration group ($1.2 \rightarrow 0.7 \rightarrow 1.1 \rightarrow 1.0$ time). However, no significant difference was observed between the two groups.
Figure 7:
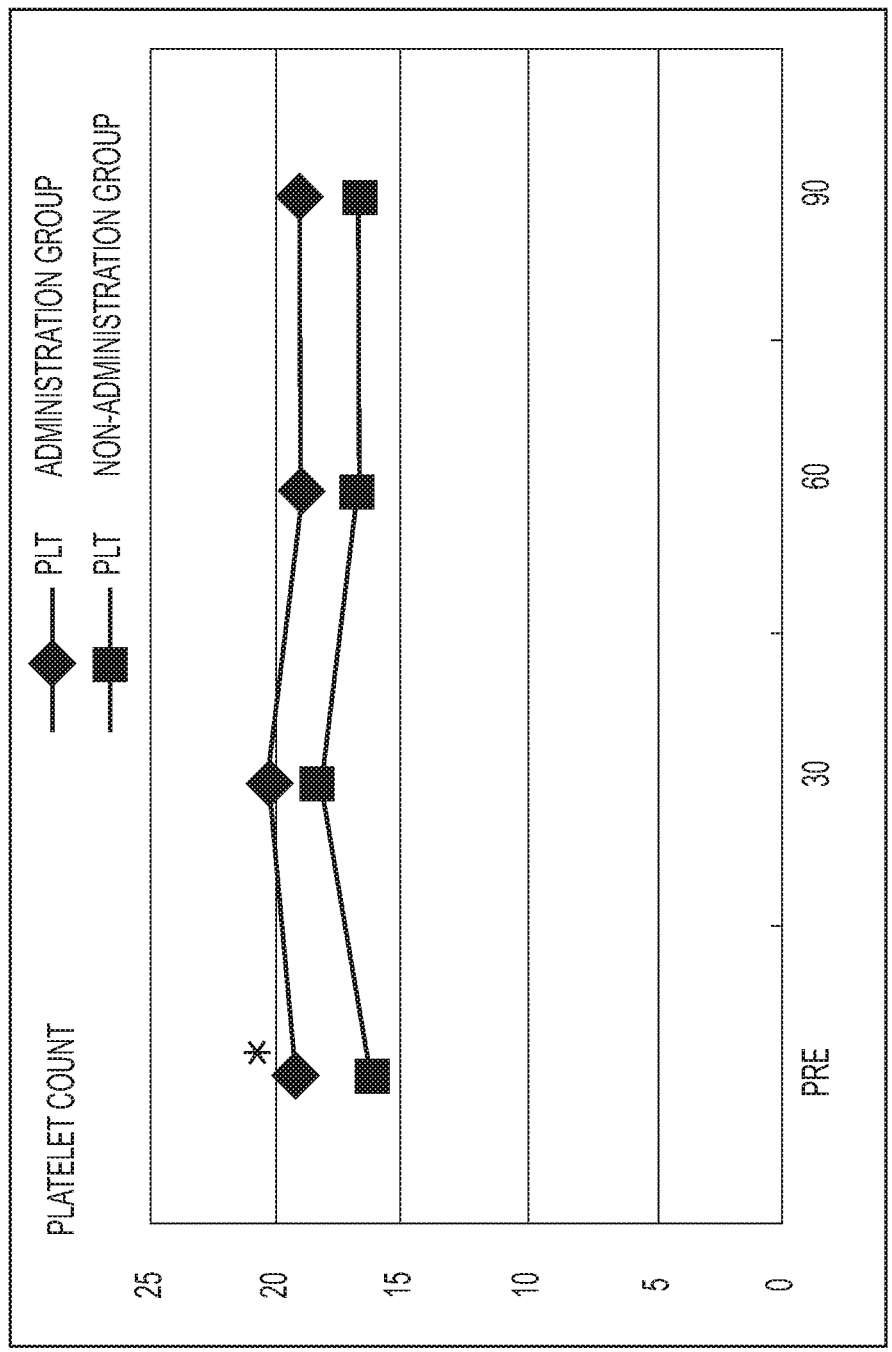
FIG. 7 shows the results of measurement of the platelet count (PLT). A diamond ♦ represents the administration group, and a square ■ represents the non-administration group. Measurement values were averaged out for each group and the values thus obtained were graphed. The vertical axis represents the platelet count ($\times 10^4$/µl), and the horizontal axis represents the number of days elapsed. A standard platelet count is 14.0 to $36.0 \times 10^4$ thousand/µl. The baseline PLT count in the administration group was significantly higher ($p<0.05$) than in the non-administration group. However, both groups showed a similar tendency, with no major change observed.
Figure 8:
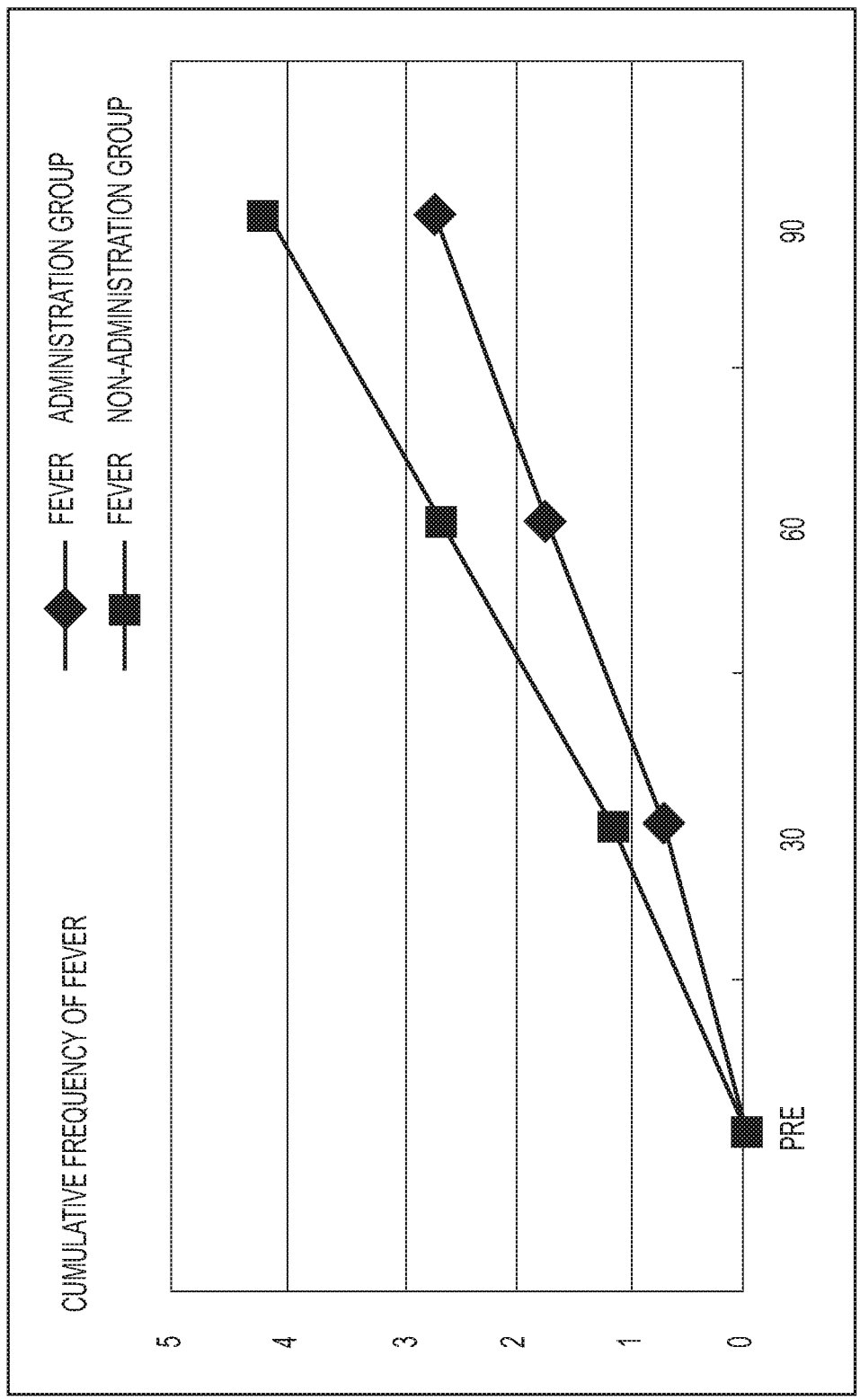
FIG. 8 shows the results of measurement of cumulative frequency of fever. A diamond ♦ represents the administration group, and a square ■ represents the non-administration group. The average cumulative frequency of fever was graphed. The vertical axis represents the cumulative frequency of fever (the number of times), and the horizontal axis represents the number of days elapsed. The non-administration group exhibited an increasing tendency in the cumulative frequency of fever as compared with the administration group.
Figure 9:
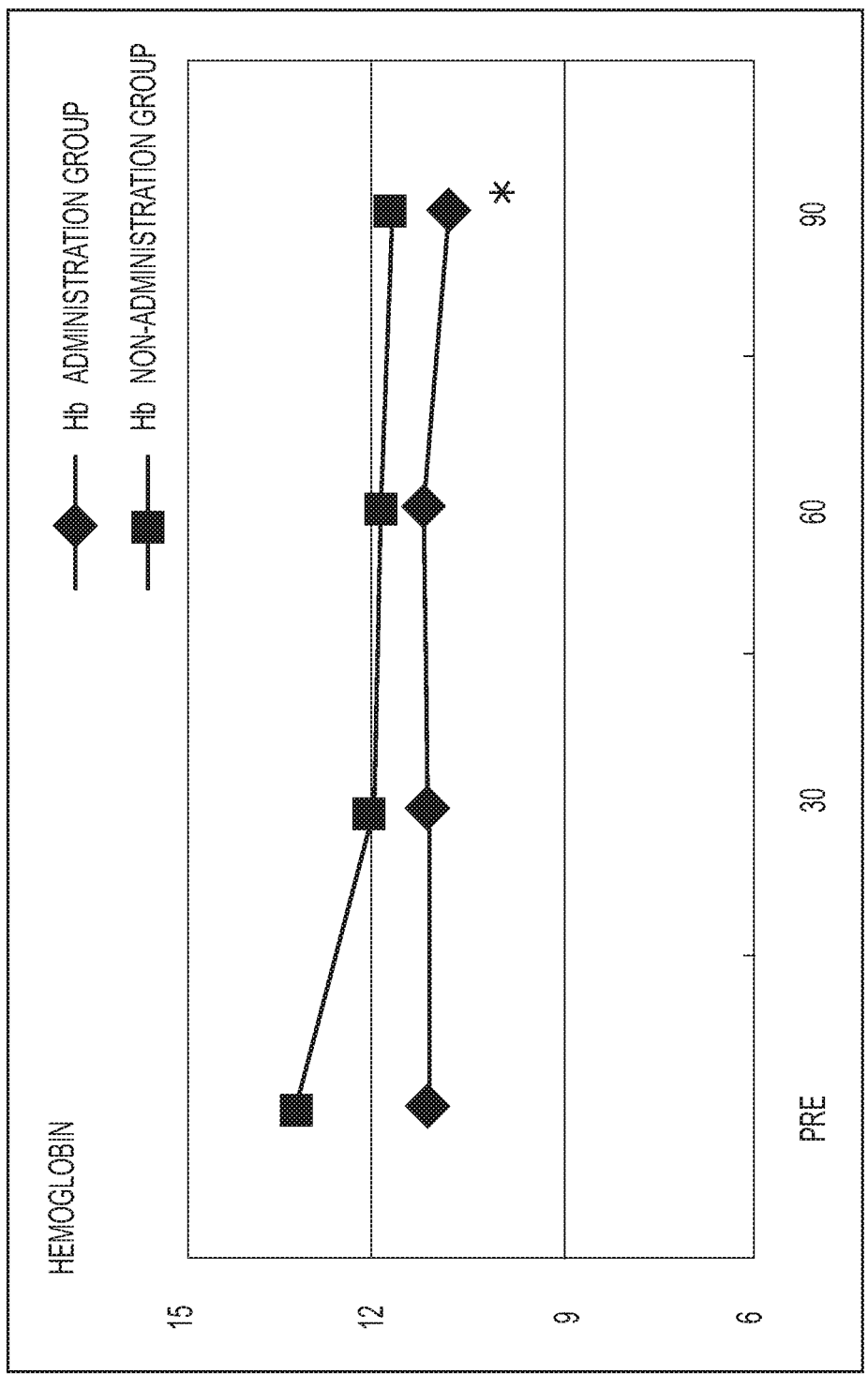
FIG. 9 shows the results of measurement of hemoglobin (Hb). A diamond ♦ represents the administration group, and a square ■ represents the non-administration group. Measurement values were averaged out for each group and the values thus obtained were graphed. The vertical axis represents the hemoglobin concentration (g/dl), and the horizontal axis represents the number of days elapsed. A standard hemoglobin concentration is 13.2 to 17.6 g/dl for males (M), and 11.3 to 15.2 g/dl for females (F). A decreasing tendency was exhibited in the non-administration group, whereas almost no change was exhibited in the administration group. However, the hemoglobin concentration in the administration group was lower than that in the non-administration group.
Figure 10:
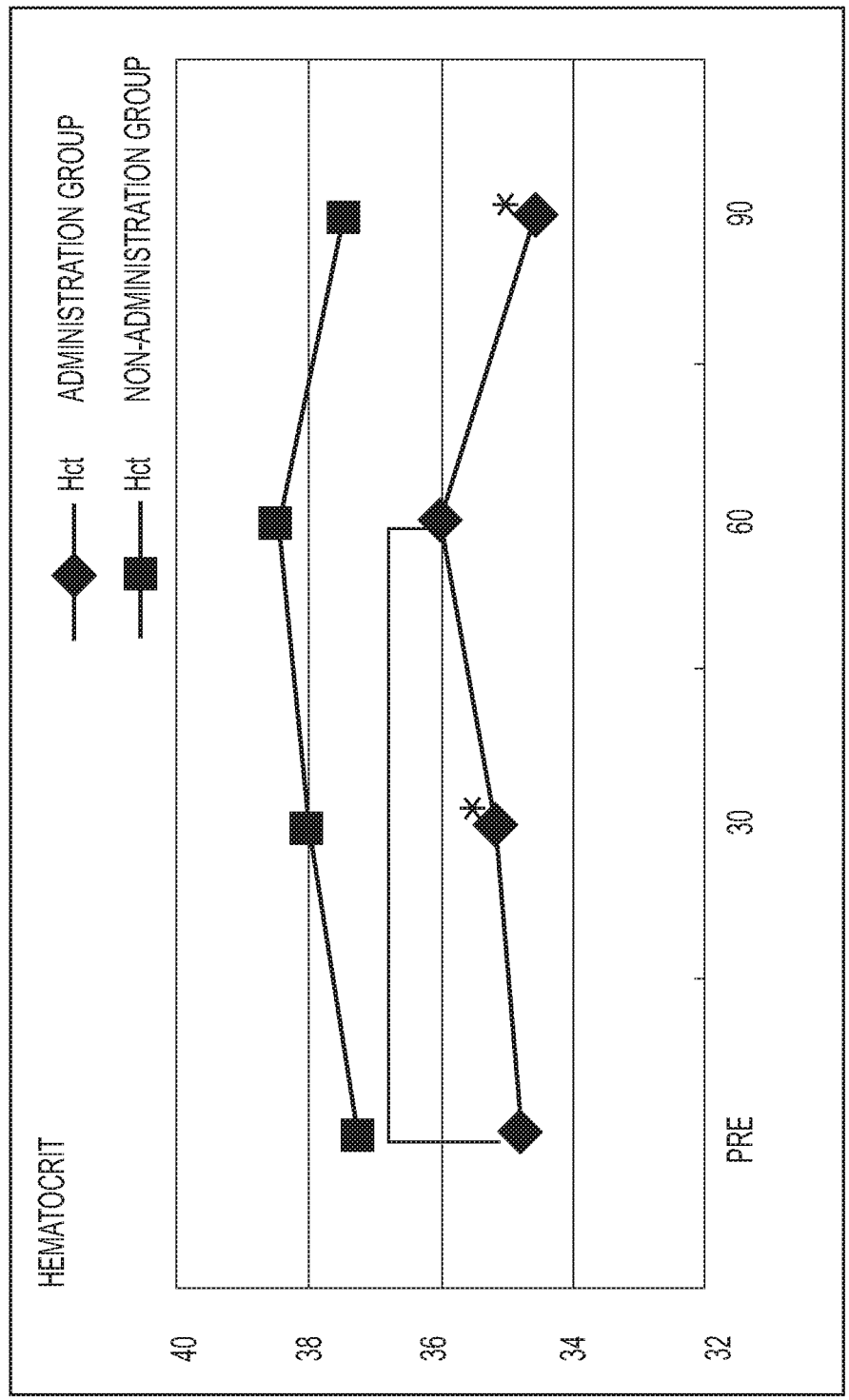
FIG. 10 shows the results of measurement of hematocrit (Ht). A diamond ♦ represents the administration group, and a square ■ represents the non-administration group. Measurement values were averaged out for each group and the values thus obtained were graphed. The vertical axis represents the hematocrit level (%), and the horizontal axis represents the number of days elapsed. A standard hematocrit level is 39.2 to 51.8% for males (M), and 33.4 to 44.9% for females (F). The baseline hematocrit level in the administration group tended to be lower than in the non-administration group. However, the hematocrit level was significantly increased ($p<0.05$) at day 60 in the administration group as compared with the baseline.
Figure 11:
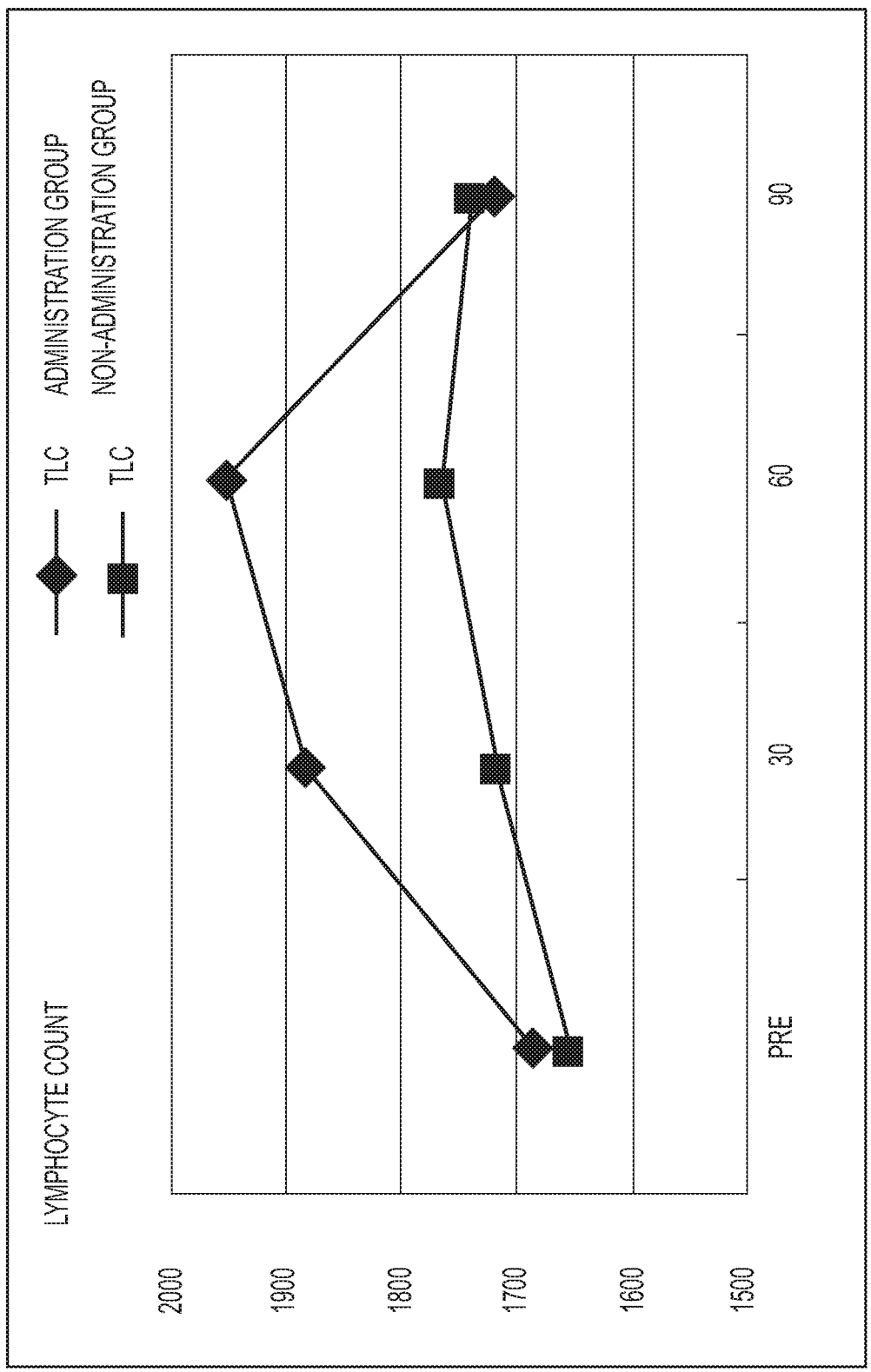
FIG. 11 shows the results of measurement of the lymphocyte count (TLC). A diamond ♦ represents the administration group, and a square ■ represents the non-administration group. Measurement values were averaged out for each group and the values thus obtained were graphed. The vertical axis represents the total lymphocyte count ($/\mu l$), and the horizontal axis represents the number of days elapsed. A standard lymphocyte count is 1500 to 4000/$\mu l$. An increasing tendency was exhibited at day 30 and day 60 in the administration group as compared with the baseline.
Figure 12:
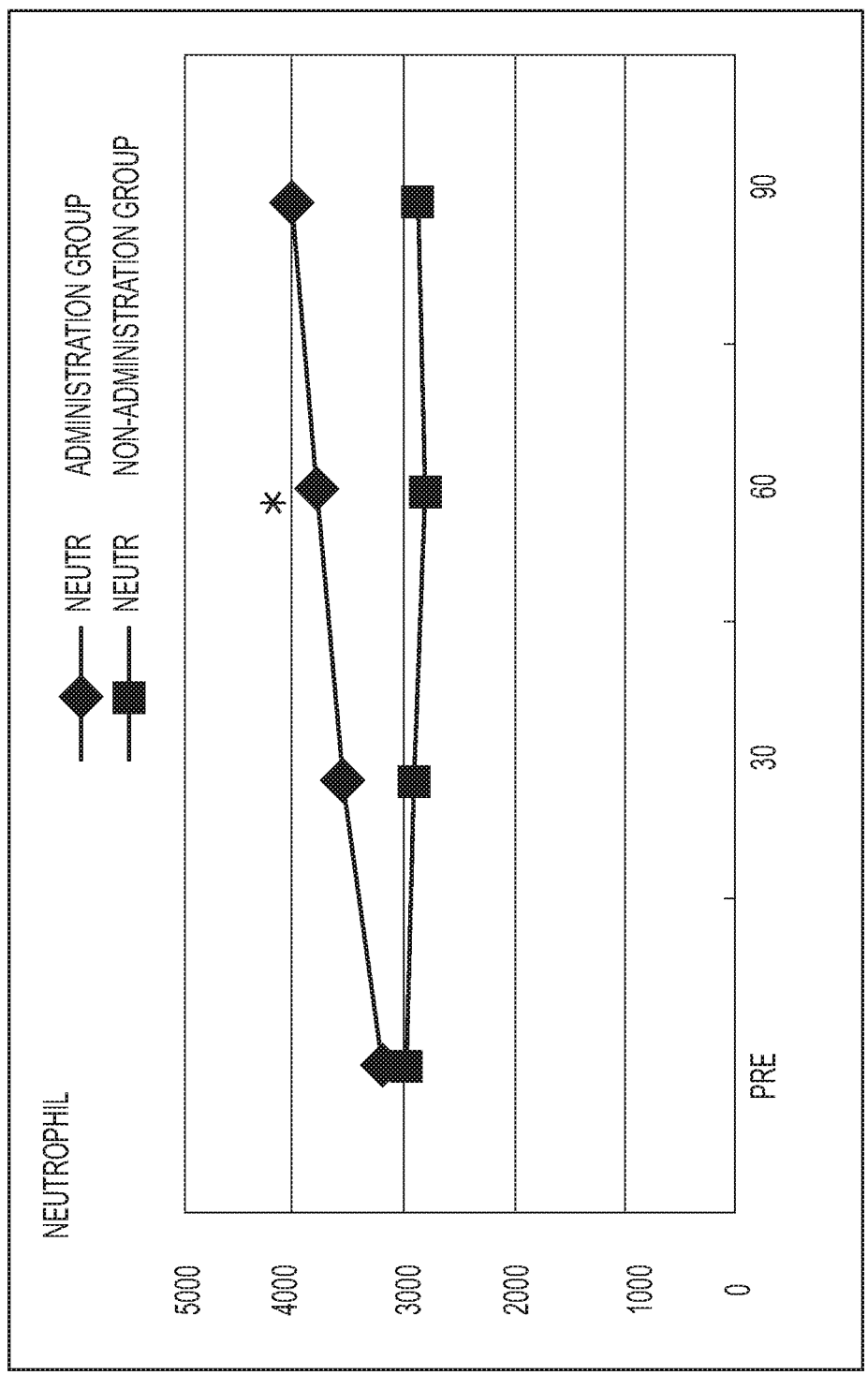
FIG. 12 shows the results of measurement of the neutrophil count (NEUTR). A diamond ♦ represents the administration group, and a square ■ represents the non-administration group. Measurement values were averaged out for each group and the values thus obtained were graphed. The vertical axis represents the neutrophil count ($/\mu l$), and the horizontal axis represents the number of days elapsed. A standard neutrophil count is 1830 to 7250/$\mu l$. While almost no change was observed in the non-administration group, an increasing tendency was exhibited in the administration group. At day 60, the neutrophil count was significantly increased ($p<0.05$) with respect to the non-administration group.

The results thus obtained are shown in FIGS. 1 to 12. There were 31 cases in the administration group (9 males and 22 females), and 23 cases in the non-administration group (6 males and 17 females). Also, BMI was 18.5 in the administration group and 19.7 in the control group, with no bias observed between the two groups.

Although both groups showed a slightly decreasing tendency in the total protein which was an index of nutritional status, the decrease was approximately 0.25 g/dl in the non-administration group and approximately 0.1 g/dl in the administration group. Both groups exhibited a decreasing tendency was in albumin, which was significantly decreased ($p<0.05$) in the administration group compared to the baseline. TTR was significantly increased at day 30, day 60, and day 90 in the administration group as compared with the baseline (16.3→18.4→18.9→17.8 mg/dl); however, no difference was observed between the two groups. Almost no change was observed in the two groups with respect to the red blood cell count, while the white blood cell count was significantly increased ($p<0.05$) in the administration group as compared with the baseline. Almost no change was observed in the two groups with respect to the platelet count and hemoglobin. Hematocrit was significantly increased ($p<0.05$) in the administration group. Neutrophils were significantly increased ($p<0.05$) in the administration group at day 60 of administration as compared with the non-administration group. The administration group exhibited an increasing tendency in TLC. With regard to the average frequency of fever, a decreasing tendency was exhibited in the administration group (1.2→0.7→1.1→1.0 time), whereas an increasing tendency was observed in the non-administration group (1.1→1.2→1.5→1.6 times); however, no significant difference was observed between the two groups. At day 30, day 60, and day 90, average cumulative frequency of fever changed as 0.71→1.74→2.74 times in the administration group, and as 1.17→2.65→4.17 times in the non-administration group; thus fever was less frequent in the administration group but no significant difference was observed. Correlation analysis for average cumulative frequency of fever and TTR showed a negative correlation only in the administration group.

4. Discussion and Conclusion

Based on the results thus obtained, it was suggested that administration of micronutrients improved nutritional status, and as a result, immunocompetence was increased, leading to a lower frequency of fever. Administration amounts of calories and protein are often considered to be the only matter of concern to nutritional management of the elderly; however, it is speculated that if micronutrients involved in metabolism are administered in amounts without being bound by their required levels, protein catabolism will be inhibited and protein and nucleic acid syntheses induced, with the result that blood protein is increased, leading to maintenance of biological functions. It has been considered that setting the priority of micronutrients high is absolutely necessary for nutritional management of the elderly.

All the publications, patents and patent applications cited in the present specification are incorporated herein by reference in their entirety.

INDUSTRIAL APPLICABILITY

The composition of the present invention can be used as a trace element-supplementing food for the elderly, and is useful for improving the nutritional status, reducing the frequency of fever, and/or increasing the immunocompetence of the elderly.

The invention claimed is:

1. A method for improving the nutritional status, reducing the frequency of fever, and/or increasing the immunocompetence, comprising:
  administering to an elderly subject a composition comprising the following components (a) to (g) as well as protein and carbohydrate but containing no additional lipid other than the components (a) to (g), in amounts effective for improving the nutritional status, reducing the frequency of fever, and/or increasing the immunocompetence:
  (a) an antioxidant agent;
  (b) at least one component selected from the group consisting of vitamin $B_1$, vitamin $B_2$, vitamin $B_6$, niacin, and pantothenic acid;
  (c) at least one component selected from the group consisting of folic acid and vitamin $B_{12}$;
  (d) zinc;
  (e) selenium;
  (f) galacto-oligosaccharide, potassium, calcium, magnesium, and phosphorus; and
  (g) a medium for containing the above components, wherein the medium is selected from the group consisting of a gel and a juice.

2. The method according to claim 1, further comprising:
  monitoring the level of at least one item selected from the group consisting of total protein, albumin, prealbumin, red blood cells, white blood cells, platelets, haemoglobin, hematocrit, total lymphocyte, and neutrophils in the blood of the elderly subject, with respect to a standard level,
  wherein the standard level is 6.5 to 8.2 g/dl for total protein, 3.5 to 5.0 g/dl for albumin, 10 to 40 mg/dl for prealbumin, 4.4 to 5.4 million/mm3 for male and 3.8 to 4.6 million/mm3 for female for red blood cells, 4000 to 8000/µl for 12/white blood cells, 130 thousand to 400 thousand/µl for platelets, 13.0 to 16.6 g/dl for male and 11.4 to 14.6 g/dl for female for hemoglobin, 38.0 to 48.9% for male and 34.0 to 43.9% for female for hematocrit, 1500 to 4000/µl for total lymphocyte, and 1830 to 7250/µl for neutrophils.

3. The method according to claim 1, wherein the composition is administered in the amount effective for increasing the level of prealbumin in the blood of the elderly subject.

4. The method according to claim 1, wherein the composition comprises vitamin $B_6$ in an amount from 3.0 mg to 8.0 mg in a total amount of the composition.

5. The method according to claim 1, wherein the composition further comprises vitamin $B_{12}$ in an amount from 5.0 µg to 15.0 µg in a total amount of the composition.

6. The method according to claim 1, wherein the antioxidant is vitamin C, and an amount of vitamin C in a total amount of the composition is from 300 to 1000 mg.

7. The method according to claim 1, wherein the composition comprises panthothenic acid in an amount from 5.0 mg to 50 mg in a total amount of the composition.

8. The method according to claim 1, wherein the composition is a gelled product.

9. A method for improving the nutritional status, reducing the frequency of fever, and/or increasing the immunocompetence, comprising:
  administering to an elderly subject a composition comprising the following components (a) to (g) as well as protein and carbohydrate but containing no additional lipid other than the components (a) to (g):
  (a) an antioxidant agent;
  (b) at least one component selected from the group consisting of vitamin $B_1$, vitamin $B_2$, vitamin $B_6$, niacin, and pantothenic acid;
  (c) at least one component selected from the group consisting of folic acid and vitamin $B_{12}$;
  (d) zinc;
  (e) selenium;
  (f) galacto-oligosaccharide, potassium, calcium, magnesium, and phosphorus; and
  (g) a medium for containing the above components, wherein the medium is selected from the group consisting of a gel and a juice,
  wherein the amount of protein component is 0.84 g or less per 70 mL±14 mL of the composition.

10. The method according to claim 9, further comprising:
  monitoring the level of at least one item selected from the group consisting of total protein, albumin, prealbumin, red blood cells, white blood cells, platelets, haemoglobin, hematocrit, total lymphocyte, and neutrophils in the blood of the elderly subject, with respect to a standard level,
  wherein the standard level is 6.5 to 8.2 g/dl for total protein, 3.5 to 5.0 g/dl for albumin, 10 to 40 mg/dl for prealbumin, 4.4 to 5.4 million/mm3 for male and 3.8 to 4.6 million/mm3 for female for red blood cells, 4000 to 8000/µl for 12/white blood cells, 130 thousand to 400 thousand/µl for platelets, 13.0 to 16.6 g/dl for male and 11.4 to 14.6 g/dl for female for hemoglobin, 38.0 to 48.9% for male and 34.0 to 43.9% for female for hematocrit, 1500 to 4000/µl for total lymphocyte, and 1830 to 7250/µl for neutrophils.

11. A method for improving the nutritional status, reducing the frequency of fever, and/or increasing the immunocompetence, comprising:
  administering to an elderly subject a composition comprising the following components (a) to (g) as well as protein and carbohydrate but containing no additional lipid other than the components (a) to (g), in amounts effective for increasing the level of prealbumin in the elderly subject:
(a) an antioxidant agent;
(b) at least one component selected from the group consisting of vitamin $B_1$, vitamin $B_2$, vitamin $B_6$, niacin, and pantothenic acid;
(c) at least one component selected from the group consisting of folic acid and vitamin $B_{12}$;
(d) zinc;
(e) selenium;
(f) galacto-oligosaccharide, potassium, calcium, magnesium, and phosphorus; and
(g) a medium for containing the above components, wherein the medium is selected from the group consisting of a gel and a juice,
wherein the amount of protein component is 0.84 g or less per 70 mL±14 mL of the composition.

12. The method according to claim 11, further comprising:
monitoring the level of at least one item selected from the group consisting of total protein, albumin, prealbumin, red blood cells, white blood cells, platelets, haemoglobin, hematocrit, total lymphocyte, and neutrophils in the blood of the elderly subject, with respect to a standard level,
wherein the standard level is 6.5 to 8.2 g/dl for total protein, 3.5 to 5.0 g/dl for albumin, 10 to 40 mg/dl for prealbumin 4.4 to 5.4 million/mm3 for male and 3.8 to 4.6 million/mm3 for female for red blood cells, 4000 to 8000/µl for 12/white blood cells, 130 thousand to 400 thousand/µl for platelets, 13.0 to 16.6 g/dl for male and 11.4 to 14.6 g/dl for female for hemoglobin, 38.0 to 48.9% for male and 34.0 to 43.9% for female for hematocrit, 1500 to 4000/µl for total lymphocyte, and 1830 to 7250/µl for neutrophils.

13. A method for improving the nutritional status, reducing the frequency of fever, and/or increasing the immunocompetence, comprising: administering to an elderly subject a composition comprising: protein, carbohydrate, potassium, calcium, magnesium, zinc, selenium, vitamin $B_1$, vitamin $B_2$, vitamin $B_6$, vitamin $B_{12}$, vitamin C, niacin, folic acid, vitamin $D_3$, vitamin E, pantothenic acid, a medium selected from the group consisting of a gel and a juice, and no additional lipid, in an amount effective for improving the nutritional status, reducing the frequency of fever, and/or increasing the immunocompetence.

14. The method according to claim 13, wherein the composition further comprises phosphorus and galacto-oligosaccharide.

15. The method according to claim 13, wherein the composition further comprises phosphorus, a dietary fiber and galacto-oligosaccharide.

16. The method according to claim 13, wherein the composition further comprises phosphorus, β-carotene and galacto-oligosaccharide.

17. The method according to claim 13, wherein the composition further comprises phosphorus, a dietary fiber, β-carotene and galacto-oligosaccharide.

* * * * *